US006568245B2

(12) United States Patent
Kaufman (10) Patent No.: US 6,568,245 B2
(45) Date of Patent: May 27, 2003

(54) EVAPORATIVE ELECTRICAL DETECTOR

(75) Inventor: Stanley L. Kaufman, New Brighton, MN (US)

(73) Assignee: TSI Incorporated, St. Paul, MN (US)

( * ) Notice: Subject to any disclaimer, the term of this patent is extended or adjusted under 35 U.S.C. 154(b) by 0 days.

(21) Appl. No.: 10/098,936

(22) Filed: Mar. 13, 2002

(65) Prior Publication Data

US 2002/0132362 A1 Sep. 19, 2002

Related U.S. Application Data

(60) Provisional application No. 60/276,171, filed on Mar. 15, 2001.

(51) Int. Cl.[7] .......................... G01N 37/00; G01N 27/62
(52) U.S. Cl. ...................... 73/28.02; 73/61.71; 324/464; 324/465; 95/69; 95/79
(58) Field of Search .......................... 73/28.01, 28.02, 73/61.58, 61.59, 61.61, 865.5, 61.71; 324/464, 465; 95/69, 72, 79; 96/17

(56) References Cited

U.S. PATENT DOCUMENTS

| 5,098,657 | A | 3/1992 | Blackford et al. | 422/73 |
|---|---|---|---|---|
| 5,192,865 | A | 3/1993 | Zhu | 250/288 |
| 5,306,412 | A | 4/1994 | Whitehouse et al. | 204/299 |
| 5,374,396 | A | 12/1994 | Blackford et al. | 422/73 |
| 5,394,090 | A | 2/1995 | Wentworth et al. | 324/464 |
| 5,955,886 | A | 9/1999 | Cohen et al. | 324/464 |
| 6,003,389 | A | 12/1999 | Flagen et al. | 73/865.5 |
| 6,037,179 | A | 3/2000 | Abdel-Rahman | 436/52 |
| RE36,892 | E | 10/2000 | Apffel, Jr. et al. | 250/288 |

OTHER PUBLICATIONS

Skoog, Douglas "Principles of Instrumental Analysis", 1985, 3rd Edition, Saunders College Publishing, pp. 536–538,559, and 784–790.*

"Evolving LC: The Life of an Enabling Technology"; *Chromatography 2001*; HTTP://pubs.acs.org/journals/chromatography/chap1.html; pp. 1–13.

"Performing Under Pressure: The Rise of Each HPLC"; *Chromatography 2001*;HTTP://pubs.acs.org/journals/chromatography/chap4.html; pp. 1–12.

"Introduction Color Writing"; *Chromatography 2001*; HTTP: //pubs.acs.org/journals/chromatography/introduction.html; pp. 1–2.

"Field–Flow Fractionation; An Outstanding Separation Technique for Supra Molecular Species"; HTTP://www-.geocities.com/capecanaveral/1475/fff.html.; pp. 1–7.

* cited by examiner

*Primary Examiner*—Robert R. Raevis
*Assistant Examiner*—Michael Cygan
(74) *Attorney, Agent, or Firm*—Larkin, Hoffman, Daly & Lindgren, Ltd.; Frederick W. Niebuhr, Esq.

(57) ABSTRACT

An aerosol detector, particularly well suited for liquid chromatography applications, includes a corona discharge source controlled to selectively charge the non-volatile residue particles of an aerosol. The aerosol initially is composed of droplets of a liquid sample, with the residue particles resulting from droplet evaporation. The selectively charged residue particles, each carrying a charge in proportion to its size, are collected at a conductive filter. The electrical current along a conductor coupled to the filter is measured repeatedly or continuously to provide an indication of concentrations of the non-volatile material. Preferably, a pneumatic nebulizer is used to generate the aerosol. When used in a liquid chromatography system, the detector can yield several separated areas of relatively high electrical current, corresponding to concentrations of several different analytes in the liquid sample.

56 Claims, 9 Drawing Sheets

VALVE POSITIONS: LOOP FILL - - - - - - - -
RUN ————

Fig.-9  10 ng INJECTIONS

Fig.-10  10 ug INJECTIONS

Fig.-11 100 ug INJECTIONS

Fig.-12 1 mg INJECTIONS AT 10 AND 20 SEC

Fig.-13 FITTED SLOPE=1.62

EVAPORATIVE ELECTRICAL DETECTOR

This application claims the benefit of priority based on Provisional Application No. 60/276,171 entitled "Evaporative Electrical Detector for HPLC and Related Separation Techniques," filed Mar. 15, 2001.

BACKGROUND OF THE INVENTION

The present invention relates to devices and processes for determining concentrations of analytes in liquid solutions, and more particularly to the use of such apparatus and processes in combination with high performance liquid chromatography and other analytical separation methods.

A variety of separation methods are known for analyzing solutes in liquid media, including liquid chromatography, high performance liquid chromatography (HPLC), gel permeation chromatography capillary electrophoresis, centrifugation, and field flow fractionation. In all of these methods, it is essential to determine concentrations of analytes in the solution under study. Further, the ability to track changes in concentrations over time, corresponding to different regions or locations within a solvent eluting from a separation column, plays a key role in identifying the solutes involved. More particularly, these analytical systems typically employ detectors capable of generating a signal that varies with analyte concentration, yielding a chromatogram or plot of concentration verses time. Because different analytes (solutes) tend to travel through the separation column at different rates as the solution passes therethrough, different solutes exit the separation column at different times. Accordingly, regions of relatively high concentrations, temporally separated on the chromatogram, indicate the presence of several different solutes. In addition, each such region on the chromatogram corresponds to a region within the solution, in terms of differences in the time each such region exits the separation column. Such exit times are useful in identifying the solutes involved.

Generally, the detectors used in analytical separation systems are of two types: Selective detectors and universal detectors. Selective detectors respond only to a specific analyte or type of analyte. For instance, an ultraviolet absorbance detector responds only to molecules capable of absorbing ultraviolet light, e.g. proteins. An example of a universal detector is a refractive index detector, which responds to any analyte capable of changing the refractive index of the liquid that contains it.

One type of universal detector, introduced relatively recently but rapidly gaining acceptance for HPLC applications, is known as the evaporative light scattering detector (ELSD). This type of detector includes a nebulizer receiving a solution eluting from a separation column, then atomizing and spraying the solution as droplets, which dry to form residue aerosol particles. An air stream carries the residue particles past a beam of light, each particle scattering (reflecting or refracting) the light as it intersects the beam. One or more photodetectors sense the scattered light. The scattered light intensity increases with the size of the particle. Accordingly, the amplitude of the photodetector output signal is used to measure particle size.

Particle size is useful in determining concentration of the material forming the particle. If the nebulizer in the ELSD generates droplets at a constant size, the diameters of the resulting aerosol particles are proportional to the cube-root of the concentration. The intensity of scattered light is approximately proportional to the sixth power of the particle diameter for particles smaller than the wavelength of the coherent energy. Intensity is approximately proportional to the second power of the particle diameter for particles larger than that wavelength. The intensity/diameter relationship between these regions is complex. Thus, for small concentrations, the scattered light intensity is proportional to the square of the analyte concentration, while for high concentrations the scattered light intensity is proportional to concentration to the $2/3$ power. With low concentrations being of primary interest in typical applications, the relationship of most concern is a variance of the output signal representing scattered light intensity as the square of the analyte concentration.

The ELSD is more sensitive than other universal detectors such as refractive-index detectors and viscosity detectors. Further, the ELSD responds to certain analyte molecules, such as polymers and carbohydrates, that do not provide a good ultraviolet or visible absorption signal. However, because of the square-law relationship just mentioned, the photomultiplier tube output signal rises rapidly with increasing concentration. As a result, the limited ranges over which photomultiplier tubes can operate impose severe limitations upon the dynamic range of the ELSD in terms of concentration measurements. ELSD systems can employ alternative detectors in lieu of photomultipliers. Nonetheless, the wide range of light intensities taxes the capabilities of these alternative detectors and the accompanying measuring circuitry. The practical dynamic range of an ELSD, in terms of a ratio of the highest measurable concentration to the lowest measurable concentration, is about 500.

A further problem associated with evaporative light scattering detectors is that the detector response is determined in part by the optical properties of the residue particles. In many cases these properties are largely unknown, requiring calibrations for each analyte under study.

In connection with analytical separation methods such as high performance liquid chromatography, but also more generally in the analysis of solutions as to the solutes they contain and their respective concentrations, it is an object of the present invention to provide a detector with a sensitivity at least comparable to the ELSD, which overcomes the aforementioned difficulties of the ELSD.

Another object is to provide a non-volatile analyte concentration detector with an enhanced dynamic range.

A further object is to provide a detector for determining analyte concentrations, with an output that varies with analyte concentrations according to a simpler relationship.

Another object is to provide a more compact instrument for measuring non-volatile analyte concentrations.

Yet another object is to provide a process for detecting concentrations of non-volatile analytes, for providing concentration measurements unaffected by the optical properties of the analyte particles involved.

SUMMARY OF THE INVENTION

To achieve these and other objects, there is provided a non-volatile analyte concentration detector. The detector includes an enclosure that defines a chamber. A first fluid passage is disposed to receive an aerosol stream composed of liquid droplets containing non-volatile material and suspended in a carrier gas. The first fluid passage is adapted to guide the aerosol stream toward the chamber as the liquid droplets substantially evaporate. As a result the aerosol stream as it enters the chamber is composed of reside particles of the non-volatile material. An ion generator is disposed near the chamber and adapted to generate multiple ions. A second fluid passage guides a gas flow toward the chamber and past the ion generator. The gas flow entrains at least a portion of the ions and carries the entrained ions into the chamber to merge with the aerosol stream, thus to apply a size-dependant electrical charge to each of the residue particles. The first and second fluid passages include respective first and second restrictions near the chamber to accelerate the aerosol stream and ion-carrying gas flow as they enter the chamber. A charge-responsive device is disposed downstream of an exit of the chamber to receive at least a portion of the charged residue particles. The device is adapted to generate an electrical signal having a level proportional to an aggregate charge of the received reside particles. Thus, the electrical signal indicates a concentration of the non-volatile material.

The charge-responsive device can include an electrically conductive filter adapted to entrap the reside particles, and a wire or other suitable electrical conductor electrically coupled with the filter. The level of electrical current through the conductor provides the indication of the non-volatile material concentration. Preferably the current is measured continuously, to provide a record of electrical current verses time over at least one selected time span corresponding to a selected sequence of the received residue particles. The electrical current level changes in response to changes in analyte concentration. More particularly, when the analyte concentration increases, each of the liquid droplets in the aerosol stream contains more of the non-volatile material. The residue particles that result from drying the aerosol are larger. The larger particles, when the aerosol stream merges with the ions, retain larger levels of electrical charge. The result is a more rapid accumulation of electrical charge at the filter, and a higher level of current in the conductor.

In theory, the level of charging in each particle is proportional to the particle diameter over a wide range of diameters. With concentrations being proportional to volumes as noted above, the particle charge levels, and thus the resulting conductor currents, should vary in proportion to the cube-root of the analyte concentration. Accordingly, a range in particle diameters encompassing two orders of magnitude provides a dynamic range encompassing six orders of magnitude, i.e. a factor of one million, for analyte concentrations.

In actual practice, based on a solution of sucrose in water, the detector electrical current has been found to vary more closely in proportion to the square-root of the concentration rather than the cube-root. This may be caused by coagulation in the aerosol, effects of analyte concentration on nebulizer performance, or other factors presently unknown. The resulting dynamic range, while not matching theoretical expectations, is a considerable improvement over the range afforded by the ELSD.

In a particularly useful application involving evaporative and electrical components, the analyte concentration detector is coupled to a nebulizer, with the first fluid passage receiving the nebulizer output. Either a pneumatic nebulizer or an electrostatic nebulizer may be employed. In the case of the electrostatic nebulizer, the aerosol leaving the nebulizer is neutralized before it is provided to the chamber for merger with the ions.

Another application of the invention, which presently is expected to gain widespread acceptance, is a high performance liquid chromatography system, in which the nebulizer receives a liquid sample from a liquid chromatography column or other separator. Upstream in the liquid chromatography system, a carrier liquid is provided to the liquid chromatography column at a substantially constant flow rate, with predetermined amounts of the liquid sample injected sequentially into the carrier liquid stream. As the liquid sample progresses through the separator, different non-volatile constituents travel through the separator at respective different rates. This tends to separate the liquid sample into regions corresponding to concentrations of the different non-volatile constituents. Alternatively, when a single non-volatile constituent is involved, different regions are characterized by different concentrations of the constituent.

When the liquid sample contains several different constituents which become concentrated within several different regions as the liquid exits the separator, a resulting record of electrical current verses time includes corresponding regions of constituent concentration, temporally separated from one another on the graph or other record to reflect the different times at which the different constituents exit the separator. Accordingly the record is useful not only for determining analyte concentrations, but also for identifying the analytes.

Further in accordance with the present invention, alternative systems can employ a variety of separators other than liquid chromatography columns. According to one alternative, field-flow fractionation, samples are injected into a flowing liquid stream. Different constituents are separated, based on different rates of travel in a transverse direction relative to the flow. In another alternative, a centrifuge is used to separate constituents based on different densities or sedimentation rates. Samples can be drawn out serially or in batches after centrifuge runs. Under another alternative, capillary electrophoresis, constituents in samples can be separated based on a variety of properties including their mobility in the liquid, size, and isoelectric points.

In accordance with any of these alternative separation methods, the system includes an analyte separator adapted to separate different non-volatile analytes in a liquid sample by concentrating different analytes primarily into different regions within the sample. In systems employing a separator that requires batch handling (e.g. a centrifuge), each sample batch is provided to the nebulizer in a manner that preserves the distinction among separate regions of the sample. Alternatively, separate regions of a sample batch can be provided to separate nebulizers.

A closely related aspect of the present invention is a process for measuring concentrations of non-volatile constituents in liquids, including:

a. providing a sample, including a liquid and at least one non-volatile constituent contained in the liquid, to a separator adapted to separate different non-volatile constituents from one another by concentrating different non-volatile constituents primarily into different regions within the sample;

b. receiving at least a portion of the sample exiting the separator, and using said portion to generate an aerosol stream composed of droplets including the liquid and the at least one non-volatile constituent;

c. allowing the liquid droplets to substantially evaporate, whereby the aerosol stream after evaporation is composed of residue particles of the at least one non-volatile constituent;

d. applying an electrical charge to each of the residual particles dependent on the residual particle's size;

e. generating an electrical signal having a level proportional to an aggregate electrical charge of a selected sequence of the electrically charged residue particles in the aerosol stream; and f. using the electrical signal to indicate a concentration of the at least one non-volatile constituent in the liquid sample over a region thereof corresponding to the selected sequence of the particles.

Thus in accordance with the present invention, solutions can be analyzed with respect to the concentrations of solutes with an accuracy comparable with that afforded by an evaporative light scattering detector, while avoiding the disadvantages associated with the ELSD. The use of electrical charge levels rather than scattered light intensity results in a considerably larger dynamic range over which concentrations can be determined with accuracy. The measurement of electrical charge (i.e. electrical current) rather than scattered light intensity also insures that concentration readings are not influenced by optical properties of the aerosol particles. For high performance liquid chromatography and a variety of other applications, the resulting concentration measurements are more reliable and can vary over a larger dynamic range.

IN THE DRAWINGS

For a further understanding of the above and features and the advantages of the invention, references made to the following detailed descriptions and to the drawings, in which.

DETAILED DESCRIPTION OF THE PREFERRED EMBODIMENTS

Figure 1:
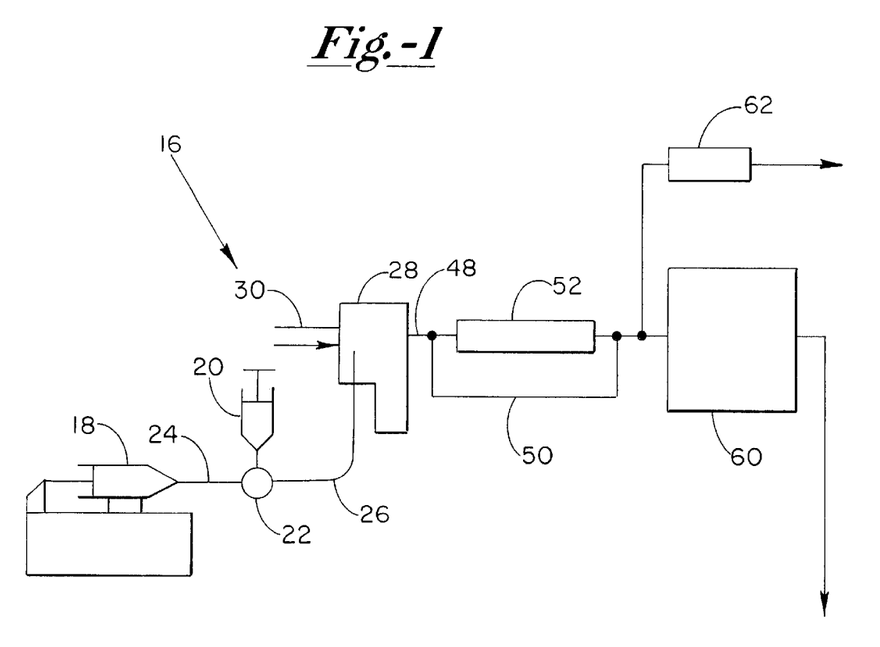
FIG. 1 is a schematic view of an analyte concentration measuring system constructed in accordance with the present invention.

Turning now to the drawings, there is shown in FIG. 1 a non-volatile residue concentration measuring system 16 for determining concentrations of solutes in liquid samples. The system includes a syringe pump 18 for providing a carrier liquid in a substantially laminar flow at a desired constant flow rate. For example, the carrier liquid can be distilled water provided at a rate of 0.59 ml per minute.

Downstream of the syringe pump is a syringe 20 containing the sample or solution to be tested. The solution is injected into the carrier liquid stream at a 20 microliter stainless steel injection loop 22. A length of PEEK tubing 24 directs the carrier liquid to the injection loop.

Syringe 20 injects the solution substantially instantaneously, each injection lasting only a fraction of a second and forming a plug of the sample that flows with the water or other carrier liquid. The plugs of solution and the carrier liquid travel through a length of PEEK tubing 26 to a pneumatic nebulizer 28. Simultaneously, compressed air is supplied to the nebulizer through an air conduit 30. The liquid flow remains essentially laminar. Accordingly, the length of tubing 26 preferably is kept as short as practicable, to preserve the separation of the sample plugs from the carrier liquid and to minimize any broadening or "tailing" of peaks indicating non-volatile residue concentrations.

Figure 2:
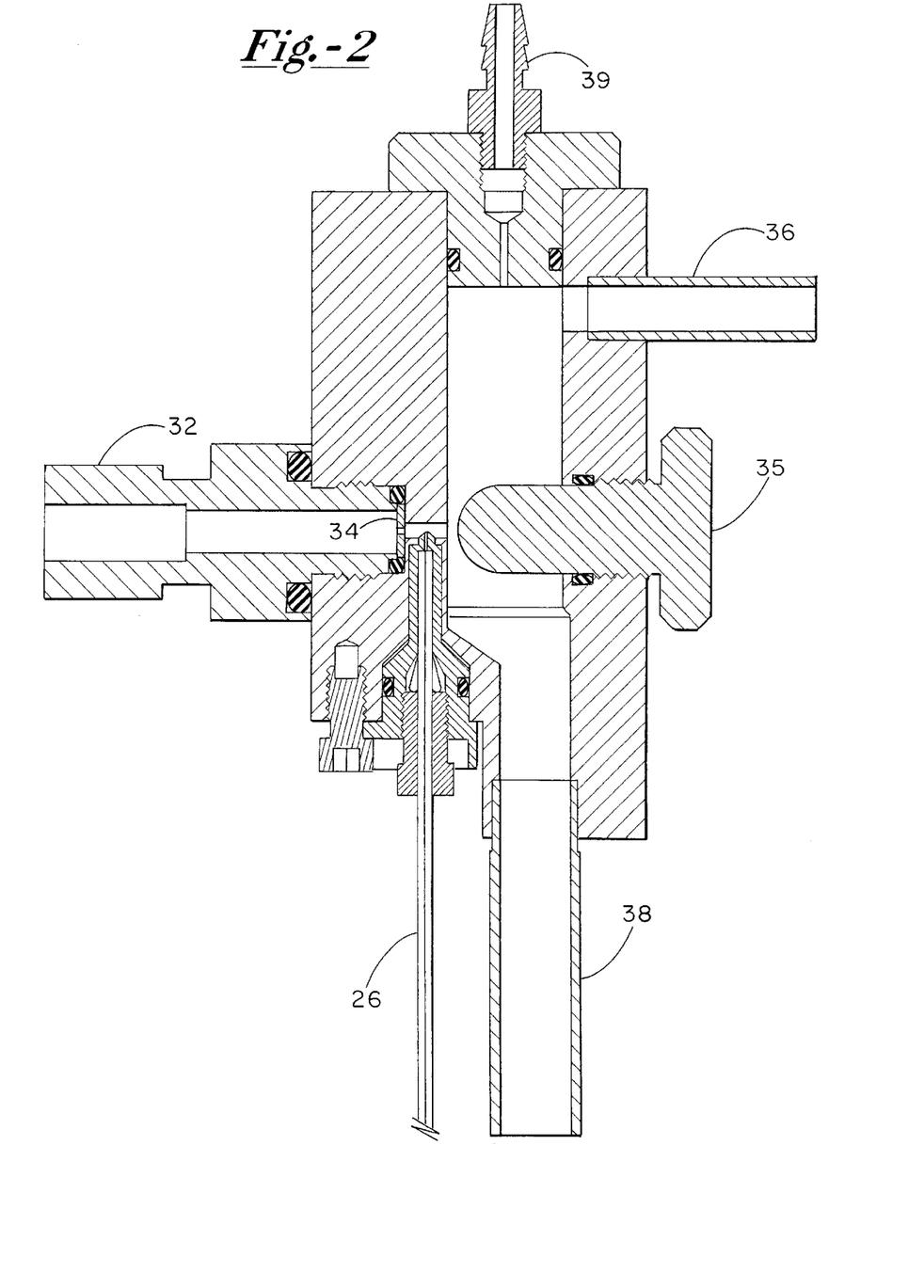
FIG. 2 is an enlarged view of part of the system in FIG. 1, namely a nebulizer.
Figure 3:
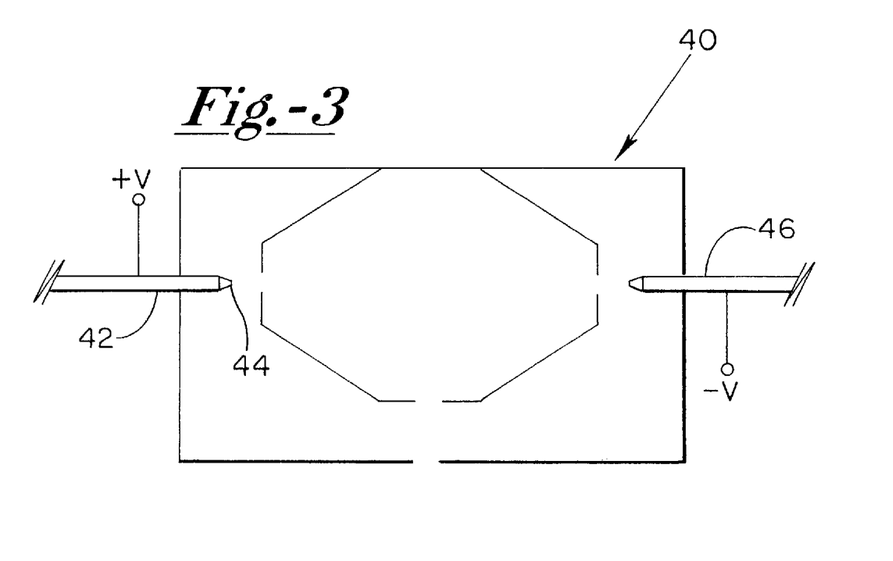
FIG. 3 is an enlarged view of a nebulizer for an alternative embodiment concentration measurement system.
Figure 4:
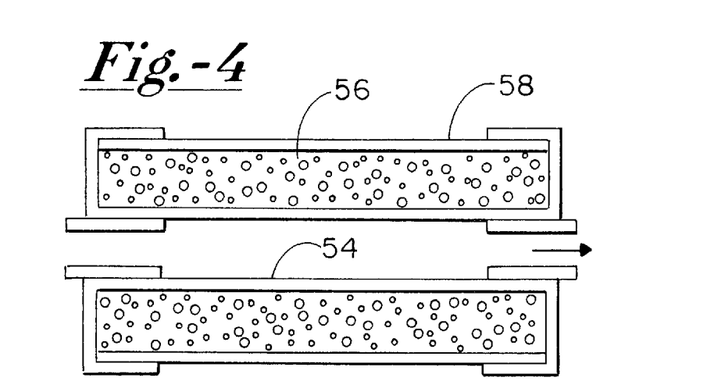
FIG. 4 is an enlarged view of a diffusion dryer of the system shown in FIG. 1.

Nebulizer 28 is shown in greater detail in FIG. 2. The nebulizer includes a fitting 32 with a passage for receiving compressed air from conduit 30. Beyond the passage is a disk 34 with a small (0.0135 inch diameter) opening. A truncated conical tip of tubing 26 extends upwardly into a passageway downstream of disk 34, where the liquid encounters the compressed air. The air moves at a speed sufficient to nebulize the liquid into multiple droplets. An impactor 35 is positioned in front of the droplet jet, to encounter and remove larger droplets. This insures that the droplets leaving the nebulizer are sufficiently small to evaporate quickly. Some of the droplets form an aerosol that travels upwardly, then horizontally, leaving the nebulizer through an exit 36. At the opposite end of the nebulizer is an exit 38 for draining excess liquid. A vent tube 39 is provided for pressure equalization with exit 38.

FIG. 3 illustrates an alternative nebulizer, namely an electrostatic nebulizer 40 incorporating an electrospray capillary 42 including a tip 44 electrically biased for an electrostatic generation of multiple droplets. The nebulizer also includes a corona discharge needle 46, oppositely biased to generate multiple ions which encounter the aerosol and tend to neutralize the aerosol droplets. For a further explanation of this type of nebulizer, reference is made to U.S. patent application Ser. No. 09/596,159 entitled "Aerosol Charge Adjusting Apparatus Employing a Corona Discharge," assigned to the assignee of this application.

Other types of nebulizers may be used in system 16, e.g. thermospray nebulizers, ultrasonic nebulizers, and hybrid devices like electrically-assisted pneumatic nebulizers.

Returning to FIG. 1, the aerosol droplets from nebulizer 28 proceed along a length of electrically conductive (e.g. stainless steel) tubing 48, at a rate of about three liters per minute in system 16. As the droplets proceed along the tubing they evaporate, to the point where the aerosol, rather than being composed of the liquid droplets, is composed of residue particles of a non-volatile material formerly dissolved in the solution.

System 16 provides two alternative paths for the aerosol: a path 50 consisting of the electrically conductive tubing, and an alternative path incorporating a diffusion dryer 52. In typical applications dryer 52 is unnecessary, due to the tendency of the droplets to undergo substantially complete evaporation within a relatively short distance downstream of nebulizer 28. Nonetheless, system 16 includes dryer 52 to ensure a complete evaporation, so that the aerosol when encountering downstream system components is made up of the residue particles rather than the droplets.

Dryer 52, as shown in FIG. 4, can be a diffusion dryer including a tubular screen 54 surrounding a passage for the aerosol. A silica gel or other desiccant 56 surrounds the tubular screen, and in turn is surrounded by an outside wall 58.

With reference again to FIG. 1, a portion of the aerosol, e.g. at a flow rate of about 1.5 liters per minute, enters an aerosol detector 60 as an aerosol stream of the residue particles in air, with the excess aerosol vented from the system through a filter 52.

Figure 5:
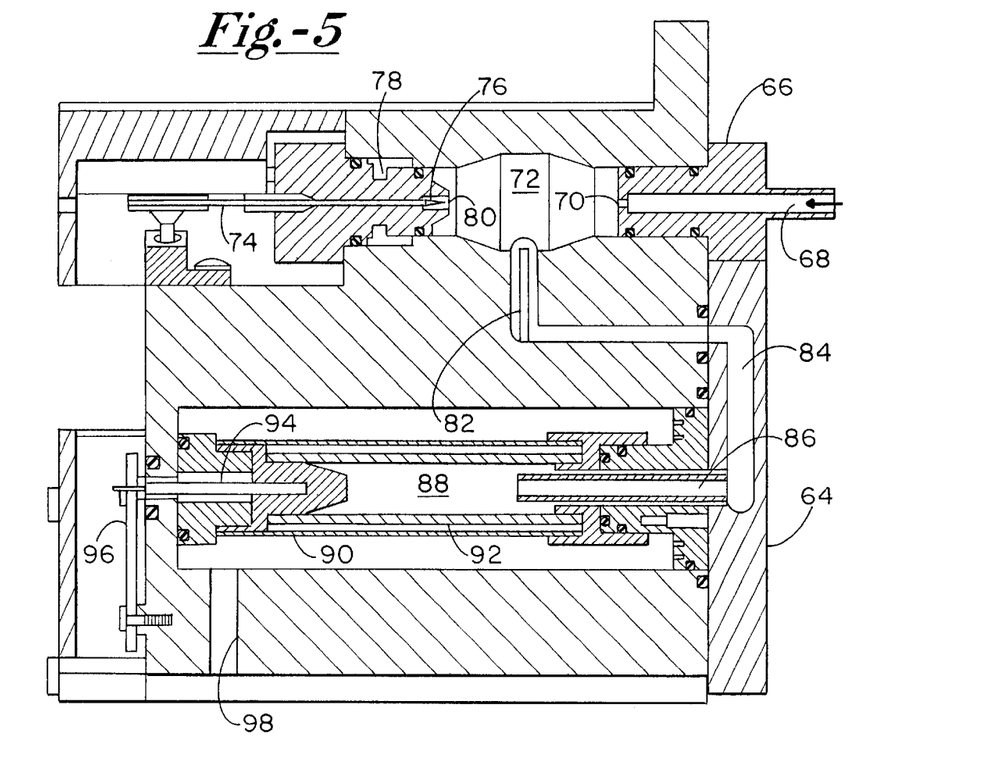
FIG. 5 is an enlarged sectional view of a detector of the system shown in FIG. 1.
Figure 6:
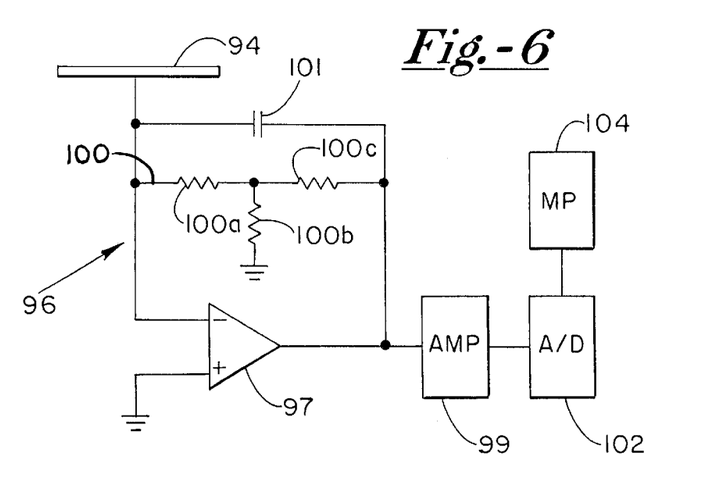
FIG. 6 is an electrical schematic view of part of the detector.
Figure 8:
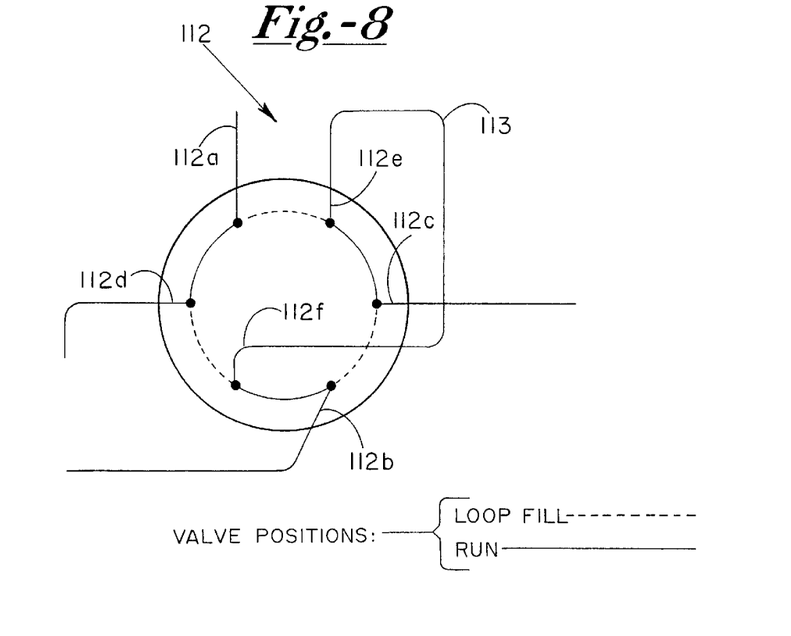
FIG. 8 is an enlarged view of a sample injection valve used in the system of FIG. 7.
Figure 9:
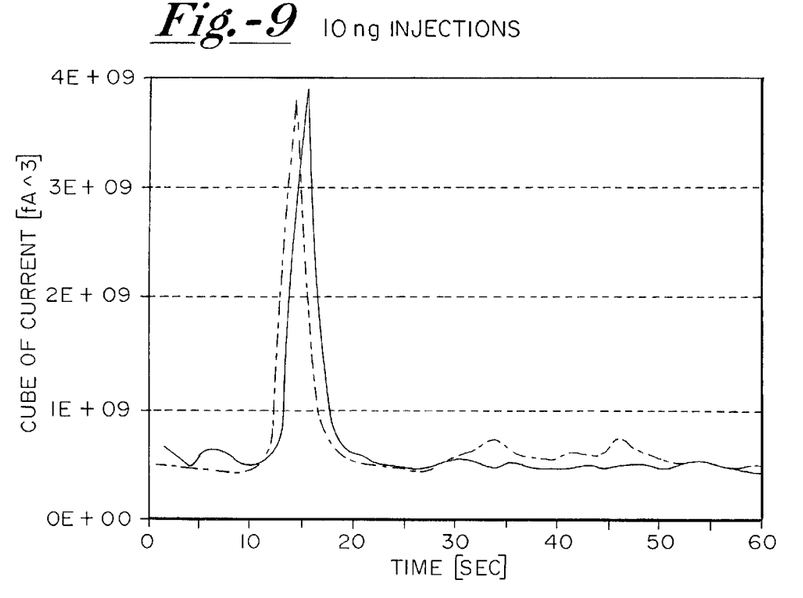
FIGS. 9–12 are plots of the cube of the electrical current measured in a system similar to that shown in FIG. 1, versus time, for several different analyte mass concentrations.
Figure 10:
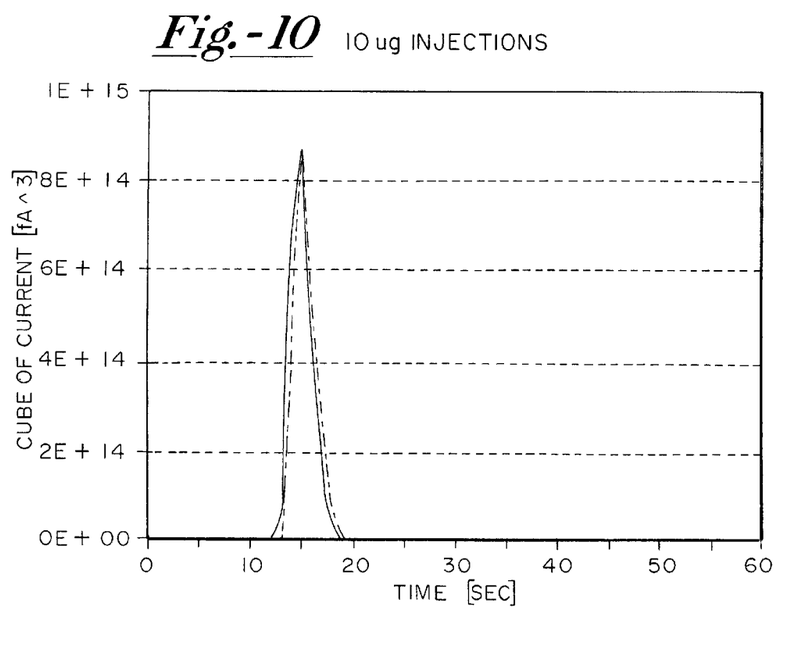
Figure 11:
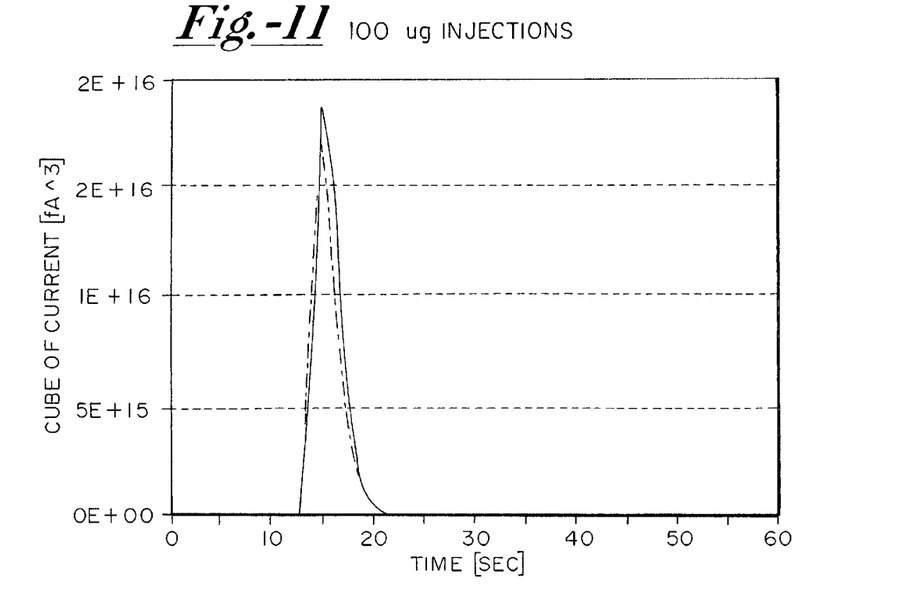
Figure 12:
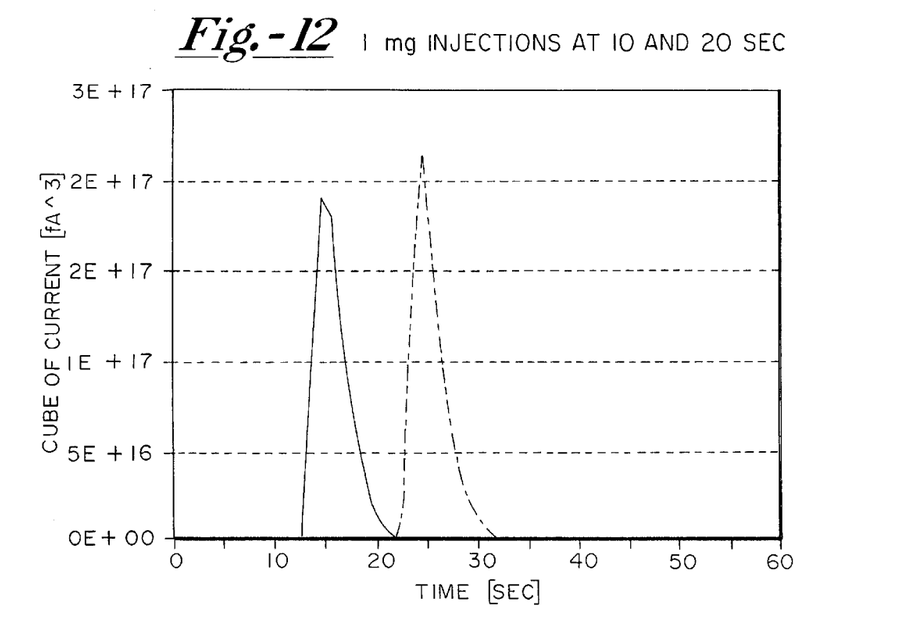

Aerosol detector 60, as seen in FIG. 5, includes an enclosure or housing 64, with a fitting 66 that incorporates a fluid passage 68 for receiving the aerosol stream into the housing. At the downstream end of the passage is a flow restriction in the form of an orifice 70 reduced in size for accelerating the aerosol stream as it enters a chamber 72, to provide an aerosol jet.

On the opposite side of the chamber is a corona discharge needle 74 having a discharge tip 76. The housing incorporates a fluid passage 78 for receiving compressed air from a compressed air source and directing the air past discharge tip 76 (FIG. 5). Meanwhile, corona discharge needle 74 is electrically biased, and generates multiple ions near the discharge tip. As the compressed air passes discharge tip 76, it entrains a portion of the ions, carrying the entrained ions to a flow restriction in the form of a reduced-size orifice 80. The compressed air accelerates as it moves through the orifice, forming an ion jet that flows counter to the aerosol jet. Both jets travel at high velocities, e.g. 40 meters per second or more. The resulting turbulent mixing of the ions and aerosol particles leads to a rapid and effective application of electrical charge to the particles. The particles are selectively charged in the sense that each particle acquires a level of charge increasing with its size. More particularly, the level of charge tends to increase substantially linearly with the diameter of the particle.

The charged particles and remaining ions leave the chamber, entering a precipitator 82 where the lighter, higher-mobility ions are removed. Beyond the precipitator, the charged aerosol proceeds along a passage 84 to an entrance 86 of an aerosol electrometer 88. The electrometer includes a wall 90 surrounding an electrically conductive filter 92. A conductor 94 is electrically coupled to the filter. A measuring circuit 96 measures current in the conductor. A passage 98 is provided for drawing air out of the electrometer.

As the aerosol enters the electrometer, the air and entrained residue particles flow toward conductive filter 92. The filter permits the passage of air, but entraps the particles. As the residue particles accumulate in the filter, the filter acquires a cumulative or aggregate charge due to the particles. Substantially simultaneously, however, the aggregate charge is drained from the filter through conductor 94 in the form of an electrical current flowing from the charged filter to a location maintained at ground.

Typically, the accumulation of charge in filter 92 and the electrical current through conductor 94 rapidly balance one another to achieve a steady state in which the level of the electrical current indicates the concentration of the non-volatile material in the solution. As previously noted, the charged residue particles exhibit a substantially linear relationship between level of charge and diameter. The cumulative or aggregate charge in filter 92 likewise varies substantially linearly with the size of the particles. The current in conductor 94 varies linearly with the aggregate or cumulative charge. More precisely, the level of current varies substantially linearly with a rate at which the residue particles are charging filter 92. Finally, given that the concentration of non-volatile material tends to vary linearly with residue particle volume, the current in conductor 94 tends to vary linearly with the cube-root of non-volatile material concentration, and thus provides an indication of that concentration.

In certain applications a Faraday cage may be used instead of filter 92 to receive (but not necessarily collect) the charged particles. In general, the conductive filter is preferred.

FIG. 6 schematically illustrates the manner in which the accumulation of charge in the conductive filter is used to indicate levels of concentration of the non-volatile material in the solution. As previously mentioned, particles approaching filter 92 are entrapped, thus applying their individual levels of charge to the filter. The aggregate charge from the particles is drained to ground from the filter through conductor 94. Measuring circuit 96 of the electrometer is coupled to conductor 94. The measuring circuit includes an RC (resistance-capacitance) network 100 including resisters 100*a* , 100*b* and 100*c,* coupled in parallel with a capacitor 101. An electrometer amplifier 97 is coupled in parallel with the capaciter and the resisters, through its negative input. The amplifier positive input is coupled to ground. The output of amplifier 97 is provided to a buffer amplifier 99 which generates an analog signal, namely a voltage level indicating the current level in conductor 94. The voltage level is provided to an analog-to-digital converter 102, the output of which is a digital value corresponding to the current in conductor 94.

With reference to FIG. 1 as well as FIG. 6, the digital values indicating current levels are provided to a microprocessor 104, which may in turn be coupled to peripheral components such as a video display terminal and printer (not shown) to provide plots or other visual indications of non-volatile residue concentrations. As previously noted, the electrical current level does not necessarily exhibit the theoretical linear match to the cube-root of non-volatile material concentration. Accordingly, microprocessor 104 advantageously incorporates computer programs for converting electrical current levels to concentration levels, as determined by calibrating samples of various non-volatile materials.

FIG. 7 illustrates a most practical and highly useful version of the invention as presently contemplated, namely a high performance liquid chromatography separation and measurement system 106. The system employs a high performance liquid chromatography (BPLC) pump 108 in lieu of syringe pump 18, and interposes an HPLC column 110 between an injection loop valve 112 and a pneumatic nebulizer 114. The injection loop valve provides substantially instantaneous injections of the liquid sample from a syringe 116, thus injecting plugs of the liquid sample into a stream of water or another carrier liquid, as before.

As seen in FIG. 8, valve 112 has six ports: a port 112*a* for receiving the liquid sample from syringe 116; a port 112*b* for receiving the carrier liquid from pump 108; a port 112*c* for providing the liquid to separator column 110; a port 112*d* for channeling excess liquid to a drain; and ports 112*e* and 112*f* on opposite sides of a sample injection loop 113.

As is known in the art, valve 112 includes a radially inward section, rotatable relative to a radially outward valve section to provide two alternative settings, including a run setting and a loop fill setting. In the run setting, the valve forms fluid passages between ports 112*a* and 112*d,* between 112*e* and 112*c,* and between 112*b* and 112*f.* The fluid passages are indicated in solid lines. In the loop fill setting, indicated by the broken lines, valve 112 forms fluid passages between ports 112a and 112e, between ports 112b and 112c, and between ports 112f and 112d.

Initially, with valve 112 in the run setting, the carrier liquid is channeled into the valve through port 112b, through injection loop 113 from port 112f to port 112e, and then through port 112c to exit the valve. Meanwhile, the liquid sample enters the valve at port 112a and leaves the valve at 112d. In this condition, loop 113 is occupied by the carrier liquid.

To fill injection loop 113 with the liquid sample, the inward section of the valve is rotated to the loop fill setting, altering both flows. The carrier liquid is channeled from port 112b to port 112c, then out of valve 112. The liquid sample flows through port 112a, through the injection loop from port 112e to port 112f, then to the drain through port 112d. Carrier liquid remaining in loop 113 immediately after the switch to the loop fill setting precedes the liquid sample through port 112d to the drain. The liquid sample rapidly pushes the carrier liquid out of the injection loop through port 112f, thus to occupy the full volume of the injection loop.

At this point, or at any desired later time, valve 112 is returned to the run setting. The incoming liquid sample is drained through port 112d once again, while the carrier liquid is channeled into the injection loop via port 112f, pushing the liquid sample out of the loop and onward to column 110 via port 112c. The process is repeated by switching valve 112 back to the loop fill setting.

For each cycle, the size of the liquid sample plug injected into the carrier liquid stream is determined by the volume of injection loop 113. Accordingly, consecutive plugs are provided at a controlled, substantially constant volume. In addition, the timing of valve switching can be controlled to determine the timing between the consecutive plugs, to provide a desired spacing between consecutive runs of the sample through HPLC column 110.

Figure 7:
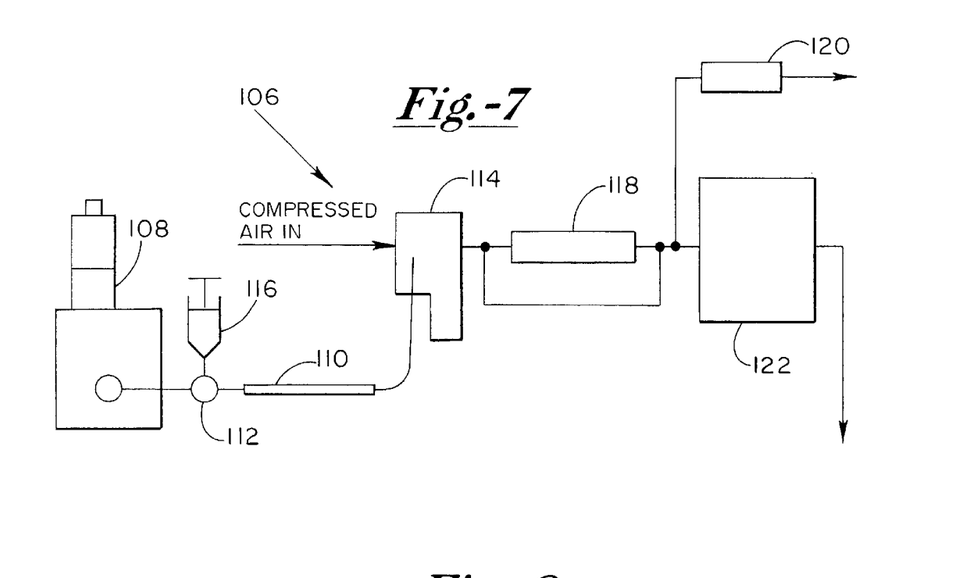
FIG. 7 is a schematic view of a high performance liquid chromatography system employing a detector in accordance with another embodiment of the invention.

Column 110 can be typical of liquid chromatography separator columns, incorporating a stationary phase and allowing the sample liquid to pass through the column as the mobile phase. As the liquid sample proceeds through the column, different non-volatile constituents travel through the column at different rates, depending largely on solubility in the stationary phase. Materials highly soluble in the stationary phase tend to travel more slowly, while materials less soluble in the stationary phase, or repelled by the stationary phase, retain higher mobility and travel more quickly through the column. As a result, the different non-volatile materials tend to become concentrated in different regions of the liquid sample as it flows through the column. As a result, the output of column 110 takes the form of distinct regions of the sample, having different concentrations of various constituents and exiting the column at different times.

Nebulizer 114, and downstream components including diffusion dryer 118, filter 120 and aerosol detector 122, can be substantially similar to their counterparts in system 16. The output of detector 122 preferably is provided to a microprocessor similar to microprocessor 104.

As the separated sample proceeds downstream of HPLC column 110, the separation of the liquid sample into distinct regions is preserved in the order of droplet generation, travel of the aerosol droplets in sequence as their evaporation yields residue particles, the travel of the residue particles generally in sequence (albeit through a turbulent mixing) in the chamber, and finally in the order in which the charged particles are captured by the electrometer filter. Accordingly, the level of the current through the counterpart of conductor 94 reflects the temporal separation of the regions of the liquid sample exiting column 110, exhibiting a higher current corresponding to higher concentrations within an initial region, a reduced current level, then an increased current level corresponding to a subsequent region of higher concentration.

The current levels generated in systems 16 and 106 preferably are tracked constantly, yielding continuous plots of electrical current level versus time or, after conversion, non-volatile material concentrations versus time.

FIGS. 9–12 are plots of the cube of the electrical current level versus time, for samples with sucrose in water reflecting injections of 10 nanograms, 10 micrograms, 100 micrograms, and 1 milligram, respectively. In all cases, especially as demonstrated by FIG. 8, the size of each peak compared to the noise level demonstrates a high level of sensitivity. Thus, highly accurate concentration measurements can be anticipated over the complete range from 10 nanograms to 1 milligram, i.e. a factor of 100,000.

Figure 13:
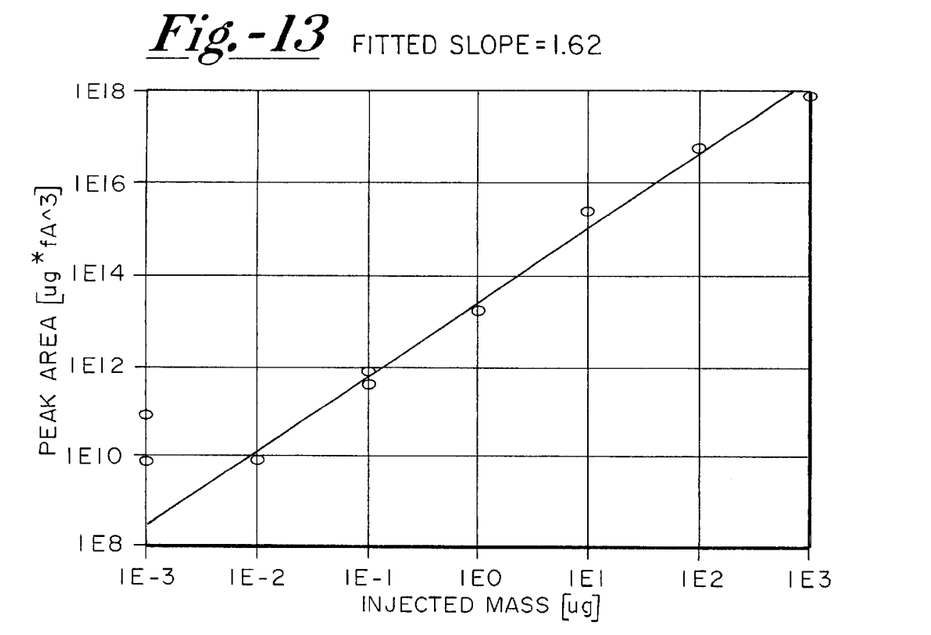
FIG. 13 is a plot of peak area versus injected mass.

The areas encompassed by the peaks increase with the injected mass, as shown in FIG. 13, a log-log plot of peak area (cube of the current) versus injected mass. The dependence indicates a 1.6 power law (slope of 1.6) rather than the theoretical 1.0, but this slope is substantially constant over the entire range of the plot. The difference may be the result of the aforementioned aerosol coagulation and analyte concentration effects, or other unknown factors.

Figure 14:
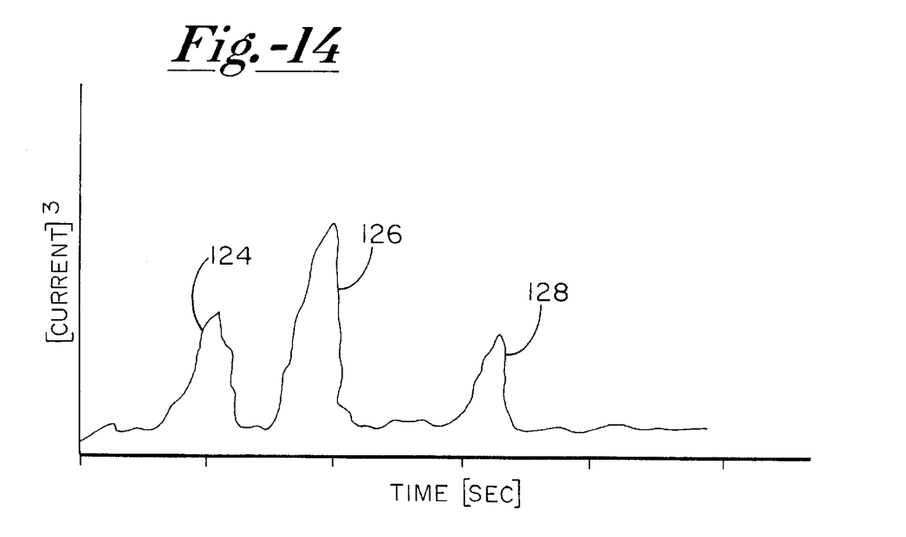
FIG. 14 is a plot showing electrical current versus time for an HPLC system of the type shown in FIG. 7.

FIG. 14 is a plot of the cube of electrical current versus time, corresponding to a possible analysis of a liquid sample of several analytes dissolved in a solvent, using system 106. The plot includes three temporally separated peaks: a peak 124 indicating a concentration of an analyte "A," a peak 126 indicating a concentration of an analyte "B," and a peak 128 indicating a concentration of an analyte "C." Analytes A, B and C can be salts, carbohydrates, proteins, lipids, or other dissolved constituents. Each of the peaks provides an indication of the concentration of the associated analyte, although calibration may be required to associate particular concentrations with the peaks. Further, the temporal positions of the peaks, both alone and with respect to one another, are useful in identifying the constituents involved.

Figure 15:
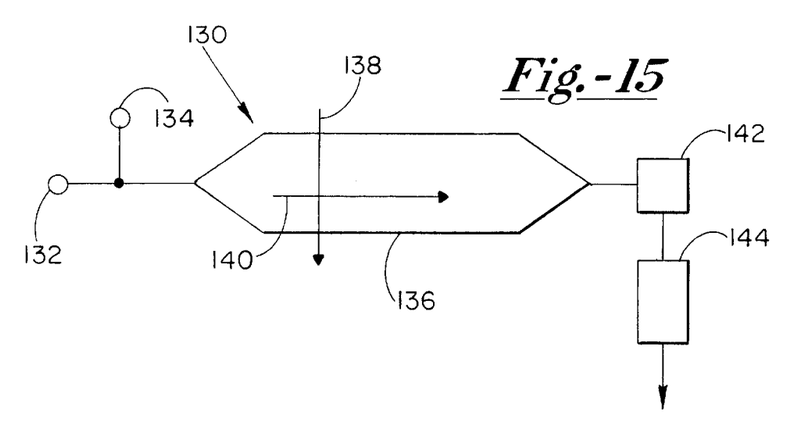
FIG. 15 is a block diagram of an alternative embodiment concentration measuring system employing field-flow fractionation.

FIG. 15 diagrammatically illustrates an alternative embodiment analyte concentration measuring system 130 including a source 132 for providing water or another carrier liquid at a substantially uniform flow rate, and a source 134 for injecting plugs of a sample liquid into the carrier liquid. The liquid proceeds to a field-flow-fractionation channel 136, along which a field is applied to the channel, acting in the direction of an arrow 138, i.e. substantially perpendicular to the flow direction indicated by an arrow 140.

In one version of system 130, the field is an acceleration due to gravity. In lieu of gravitational acceleration, channel 136 can be accelerated by spinning the channel, which in this case is preferably arcuate. In an alternative version of this system, a crossflow stream is used to apply a viscous force, capable of separating constituents by size. In yet another alternative, a temperature gradient is applied across channel 136.

In any event, the output of the channel is provided to a nebulizer 142. The nebulizer output, preferably after sufficient drying to provide an aerosol composed of residue particles, is provided to a detector 144 where the residue particles are selectively charged and accumulated as previously described.

Figure 16:
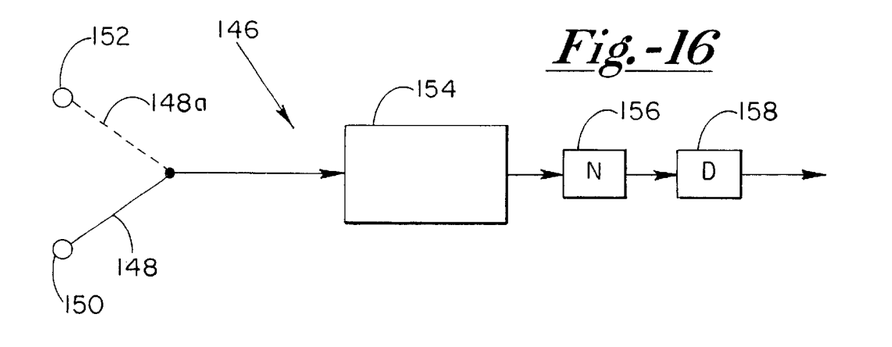
FIG. 16 is a block diagram of an alternative system employing capillary electrophoresis.

FIG. 16 illustrates an alternative system 146 employing capillary electrophoresis. As indicated by the solid line at 148 and the broken line at 148a, the system is controllable to alternatively provide a carrier liquid from a source 150, and plugs or bursts of a liquid sample from a source 152. The liquid proceeds to a separator 154 which in one version of system 146 is a length of capillary tubing. In an alternative version, separator 154 can be a glass or plastic substrate in which a plurality of flow channels are etched. This approach can be used to separate analytes based on their mobility in liquid, their size, or their isoelectric points. The separator output is provided to a nebulizer 156, preferably an electrospray nebulizer. The aerosol output of the nebulizer is provided to a detector 158.

Figure 17:
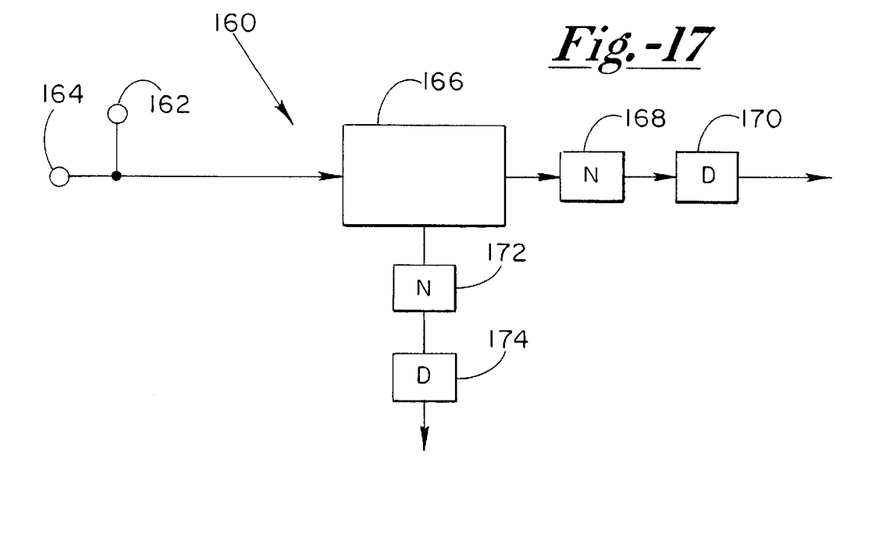
FIG. 17 is a block diagram of yet another alternative measurement system employing a centrifuge as a separator.

FIG. 17 illustrates a further alternative system 160 in which plugs or bursts of a liquid sample from a source 162 are injected into a carrier liquid flow from a source 164 on the way to a centrifuge 166. Depending on the version of this system, analytes can be separated on the basis of their densities, or their sedimentation rates. Additionally, different configurations of system 160 depend on whether centrifuge 166 accommodates a continuous flow, or processes the sample in a batch mode. In a continuous flow system, the centrifuge output is provided to a nebulizer 168, with the aerosol output of the nebulizer provided to a detector 170. Alternatively, different regions of a stratified sample can be provided sequentially to a nebulizer 172, the nebulizer in turn providing its output to a detector 174.

Thus in accordance with the present invention, liquid samples can be analyzed to determine concentrations of non-volatile materials dissolved in the liquid, with a high degree of accuracy over a wide range of concentration levels. Systems configured according to the invention measure the extent to which non-volatile residue particles are electrically charged, in lieu of measuring scattered light intensity. This considerably broadens the range over which concentration readings are reliable, and also ensures that optical properties of the particles have no influence on the results. The systems are particularly well suited for high performance liquid chromatography, and are well suited for a variety of other applications, regardless of whether they involve separating several constituents dissolved in the liquid sample.

What is claimed is:

1. A process for measuring concentrations of non-volatile constituents in liquids, including:
    providing a sample including a liquid and at least one non-volatile constituent contained in the liquid to a separator adapted to separate the different non-volatile constituents from one another by concentrating different non-volatile constituents primarily into different regions within the sample;
    receiving at least a portion of the sample exiting the separator, and using said portion to generate an aerosol stream composed of droplets including the liquid and the at least one non-volatile constituent;
    allowing the liquid to substantially evaporate, whereby the aerosol stream after evaporation is composed of residue particles of the at least one non-volatile constituent;
    after allowing the liquid to substantially evaporate, applying an electrical charge to each of the residue particles dependent on the residue particle's size;
    generating an electrical signal having a level proportional to an aggregate electrical charge of a selected sequence of the electrically charged residue particles in the aerosol stream; and
    using the electrical signal to indicate a concentration of the at least one non-volatile constituent in the liquid sample over a region thereof corresponding to the selected sequence of the charged residue particles.

2. The process of claim 1 wherein:
    the separator comprises a liquid chromatography column adapted to cause different non-volatile constituents to travel through the column at respective different rates as the sample progresses through the column, whereby the different regions of the sample exit the column at different times;
    providing a sample includes intermittently injecting the sample into a carrier liquid stream to form plugs of the sample that travel with the carrier liquid; and
    moving the sample through a separator comprises moving the carrier liquid and the plugs through the separator.

3. The process of claim 2 wherein:
    the liquid sample includes at least two different non-volatile constituents;
    the selected sequence of the electrically charged residue particles encompasses at least first and second different regions of the liquid sample corresponding to concentrations of first and second kinds of the non-volatile constituents respectively; and
    said using the electrical signal comprises indicating first and second concentrations corresponding to the first and second regions respectively.

4. The process of claim 1 wherein:
    generating the electrical signal in proportion to the aggregate electrical charge comprises using an electrically conductive component to collect the charged residue particles of the selected sequence, and sensing an electrical current along an electrical conductor coupled to the collector component.

5. The process of claim 4 wherein:
    sensing the electrical current includes continuously measuring the electrical current to provide a continuous record of the electrical current versus time over a time span corresponding to the selected sequence.

6. The process of claim 1 wherein:
    said applying an electrical charge to each of the residue particles comprises generating multiple ions, and using a gas stream to entrain and carry at least a portion of the ions into a confluence with the aerosol stream.

7. The process of claim 6 further including:
    accelerating the aerosol stream and the gas stream proximate said confluence of the gas stream with the aerosol stream.

8. A process for determining non-volatile residue concentrations, including:
    generating an aerosol stream composed of liquid droplets containing non-volatile material;
    drying the droplets, whereby the aerosol stream at a point downstream of aerosol stream generation is composed of residue particles of the non-volatile material;
    generating multiple ions, and providing a gas flow past the ions to entrain at least a portion of the ions in the gas flow to provide an ion stream;
    after drying the droplets, directing the ion stream and the aerosol stream towards one another and into a turbulent merger to promote a mixing of the ions and the residue particles to apply a size-dependent electrical charge to each of the residue particles;
    generating an electrical signal having a level proportional to an aggregate electrical charge of a selected sequence of the electrically charged residue particles in the aerosol stream; and using the electrical signal to indicate a concentration of the at least one non-volatile material in the liquid sample over a region thereof corresponding to the selected sequence of the charged residue particles.

9. The process of wherein:

said generating the electrical signal includes generating the electrical signal at a level proportional to said concentration to the "Xth" power, wherein:

$$\frac{1}{3} \leq X < \frac{2}{3}.$$

10. The process of claim 8 further including:

accelerating the aerosol stream and the ion stream proximate said turbulent merger.

11. The process of claim 8 wherein:

generating the electrical signal in proportion to the aggregate electrical charge comprises using an electrically conductive component to collect the charged residue particles of the selected sequence, and sensing an electrical current along an electrical conductor coupled to the conductive component.

12. The process of claim 11 wherein:

sensing the electrical current includes continuously measuring the electrical current to provide a continuous record of the electrical current versus time over a time span corresponding to the selected sequence.

13. The process of claim 8 wherein:

said applying an electrical charge to each of the residue particles comprises generating multiple ions, and using a gas stream to entrain and carry at least a portion of the ions into a confluence with the aerosol stream.

14. A system for analyzing liquid samples containing non-volatile analytes, including:

an analyte separator adapted to separate different non-volatile analytes in a liquid sample by concentrating the different non-volatile analytes primarily into different regions within the liquid sample;

a nebulizer disposed to receive the liquid sample from the separator, and adapted to nebulize at least a portion of the liquid sample to generate an aerosol stream composed of droplets of the liquid sample suspended in a carrier gas and containing the at least one analyte, the droplets tending to evaporate whereby the aerosol stream at a selected location downstream of the nebulizer is composed of residue particles of the at least one analyte;

an electrical charger disposed to receive the aerosol stream near the selected location and adapted to apply a size-dependent electrical charge to each of the residue particles; and a charge-responsive device disposed to receive the electrically charged residue particles and adapted to generate an electrical signal in proportion to an aggregate charge of the received residue particles and thereby indicate a concentration of the at least one analyte in the liquid over a range determined by the received residue particles.

15. The system of claim 14 wherein:

the analyte separator comprises a liquid chromatography column adapted to cause the different non-volatile analytes in the liquid sample to travel therethrough at different rates as the liquid sample flows through the column, whereby the different regions exit the column at different times.

16. The system of claim 15 further including:

a pump for providing the liquid sample to the liquid chromatography column under an elevated pressure.

17. The system of claim 15 further including:

a first liquid supply for providing a carrier liquid stream to the liquid chromatography column at a substantially constant flow rate, and a second liquid supply operable to introduce predetermined amounts of the liquid sample by injection into the carrier liquid stream.

18. The system of claim 14 wherein:

the liquid sample contains first and second different analytes substantially concentrated within respective first and second regions of the liquid sample as the liquid sample exits the liquid chromatography column; and the received residue particles include first and second temporally separated portions corresponding to the first and second regions respectively, whereby the electrical signal indicates first and second concentrations of the first and second analytes, respectively.

19. The system of claim 14 wherein:

the charge-responsive device comprises a collector for accumulating the residue particles.

20. The system of claim 19 wherein:

the collector comprises an electrically conductive filter adapted to entrap the residue particles;

the charge-responsive device further includes a conductor electrically coupled to the filter and a measuring circuit coupled to the conductor for sensing an electrical current along the conductor; and the electrical signal consists essentially of the electrical current.

21. The system of claim 20 wherein:

the measuring circuit is adapted to continually measure the electrical current to provide a continuous record of the electrical current versus time over at least one selected time span corresponding to a selected sequence of the received residue particles.

22. The system of claim 14 wherein:

the charge-responsive device includes an analog-to-digital converter adapted to convert the electrical signal to a digital value.

23. The system of claim 22 further including:

a digital processor coupled to the analog to digital converter for computing the concentration of the at least one analyte based on the digital value.

24. The system of claim 14 wherein:

the charge-responsive device comprises an electrometer.

25. The system of claim 14 wherein:

the nebulizer is selected from the group consisting of: pneumatic nebulizers, ultrasonic nebulizers, thermospray nebulizers, and electrostatic nebulizers.

26. The system of claim 14 wherein:

the electrical charger comprises an ion generator.

27. The system of claim 26 wherein:

the ion generator comprises an electrically conductive member adapted to provide a corona discharge.

28. The system of claim 14 wherein:

the electrical charger provides a unipolar charge.

29. The system of claim 14 further including:

a diffusion dryer disposed between the nebulizer and the electrical charger to facilitate evaporation of the liquid droplets as the aerosol stream proceeds toward the electrical charger.

30. The system of claim 14 wherein:
said charge-responsive device is configured to generate the electrical signal at a level proportional to said concentration to the "Xth" power, wherein:

$$\frac{1}{3} \leq X < \frac{2}{3}.$$

31. A detector for determining concentrations of non-volatile analytes in liquid solutions, including:
a nebulizer disposed to receive a liquid incorporating non-volatile material, and adapted to nebulize at least a portion of the liquid to generate an aerosol stream composed of droplets of the liquid suspended in a carrier gas, the droplets tending to evaporate whereby the aerosol stream at a selected location downstream of the nebulizer is composed of residual particles of the non-volatile material suspended in the carrier gas;
an ion generator disposed near the selected location;
a source of compressed gas for providing a gas flow, and a fluid conduit adapted to guide the gas flow past the ion generator to entrain at least a portion of the ions and carry the entrained ions into a confluence with the aerosol stream, to apply a size-dependent electrical charge to each of the residue particles; and
a charge-responsive device disposed to receive the charged residue particles and adapted to generate an electrical signal having a level proportional to an aggregate charge of the received residue particles, thereby to indicate a concentration of the non-volatile material in the liquid.

32. The detector of claim 31 wherein:
the fluid conduit is shaped to accelerate the gas flow proximate the aerosol stream, to promote a turbulent mixing of the ions and the residue particles.

33. The detector of claim 32 wherein:
the charge-responsive device comprises a collector for accumulating the residue particles.

34. The detector of claim 33 wherein:
the collector comprises an electrically conductive filter adapted to entrap the non-volatile residue particles;
the charge-responsive device further includes a conductor electrically coupled to the filter and a measuring circuit coupled to the conductor for sensing an electrical current along the conductor; and
the electrical signal consists essentially of the electrical current.

35. The detector of claim 34 wherein:
the measuring circuit is adapted to continuously measure the electrical current level to provide a continuous record of the electrical current versus time over at least one selected time span corresponding to a selected sequence of the received residue particles.

36. The detector of claim 31 wherein:
the charge-responsive device comprises an electrometer.

37. The detector of claim 31 wherein:
the charge-responsive device includes an analog-to-digital converter adapted to convert the electrical signal to a digital value.

38. The detector of claim 37 further including:
a digital processor coupled to the analog to digital converter for computing the concentration of the at least one analyte based on the digital value.

39. The detector of claim 31 wherein:
the nebulizer is selected from the group consisting of: pneumatic nebulizers and electrostatic nebulizers.

40. The detector of claim 31 wherein:
the ion generator comprises an electrically conductive member adapted to provide a corona discharge.

41. The detector of claim 31 wherein:
the electrical charger provides a unipolar charge.

42. The detector of claim 31 further including:
a diffusion dryer disposed between the nebulizer and the electrical charger to facilitate evaporation of the liquid droplets as the aerosol stream proceeds toward the electrical charger.

43. The detector of claim 31 wherein:
said charge-responsive device is configured to generate the electrical signal at a level proportional to said concentration to the "Xth" power, wherein:

$$\frac{1}{3} \leq X < \frac{2}{3}.$$

44. The detector of further including:
a means for accelerating the aerosol stream proximate said confluence to further promote said turbulent mixing.

45. A non-volatile analyte concentration detection device including:
an enclosure defining a chamber;
a first fluid passage disposed to receive an aerosol stream composed of liquid droplets containing non-volatile material and suspended in a carrier gas, said first fluid passage being adapted to guide the aerosol stream toward the chamber as the liquid droplets substantially evaporate whereby the aerosol stream as it enters the chamber is composed of residue particles of the non-volatile material;
an ion generator disposed near the chamber and adapted to generate multiple ions;
a second fluid passage for guiding a gas flow toward the chamber and past the ion generator, to entrain at least a portion of the ions and carry the entrained ions into the chamber to merge with the aerosol stream, thus to apply a size-dependent electrical charge to each of the residue particles; and
a charge-responsive device disposed downstream of an exit of the chamber to receive at least a portion of the charged residue particles and adapted to generate an electrical signal having a level proportional to an aggregate charge of the received residue particles, thereby to indicate a concentration of the non-volatile material.

46. The device of claim 45 wherein:
the first and second fluid passages include respective first and second flow restrictions near the chamber to accelerate the aerosol stream and the ion-carrying gas flow, respectively, as they enter the chamber.

47. The device of claim 45 wherein:
the charge-responsive device comprises a collector for accumulating the residue particles.

48. The device of claim 47 wherein:
the collector comprises an electrically conductive filter adapted to entrap the residue particles;
the charge-responsive device further includes a conductor electrically coupled to the filter, and a measuring circuit coupled to the conductor for sensing a level of electrical current along the conductor; and
the electrical signal consists essentially of the electrical current.

49. The device of claim 48 wherein:

the measuring circuit is adapted to continuously measure the electrical current to provide a continuous record of electrical current versus time over at least one selected time span corresponding to a selected sequence of the received residue particles.

50. The device of claim 48 further including:

an analog-to-digital converter adapted to convert the electrical current to a digital value.

51. The device of claim 50 further including:

a digital processor coupled to the analog to digital converter for computing the concentration of the at least one analyte based on the digital value.

52. The device of claim 45 wherein:

the charge-responsive device comprises an electrometer.

53. The device of claim 45 wherein:

the ion generator comprises an electrically conductive member adapted to provide a corona discharge.

54. The device of claim 45 wherein:

the electrical charger provides a unipolar charge.

55. The device of claim 43 further including:

a diffusion dryer disposed along the first fluid passage to facilitate evaporation of the liquid droplets as the aerosol stream proceeds toward the chamber.

56. The device of claim 43 wherein:

said charge-responsive device is configured to generate the electrical signal at a level proportional to said concentration to the "Xth" power, wherein:

$1/3 \leq X < 2/3$.

* * * * *

UNITED STATES PATENT AND TRADEMARK OFFICE
CERTIFICATE OF CORRECTION

PATENT NO.     : 6,568,245 B2
DATED          : May 27, 2003
INVENTOR(S)    : Stanley L. Kaufman It is certified that error appears in the above-identified patent and that said Letters Patent is hereby corrected as shown below:

Column 13,
Line 7, after "of" insert -- claim 8 --.

Column 16,
Line 19, after "of" insert -- claim 32 --.

Column 18,
Lines 6 and 10, delete "43" insert -- 45 --.

Signed and Sealed this

Sixteenth Day of September, 2003

JAMES E. ROGAN
*Director of the United States Patent and Trademark Office*